United States Patent [19]

Haga et al.

[11] Patent Number: 4,752,325
[45] Date of Patent: * Jun. 21, 1988

[54] 2-SUBSTITUTED PHENYL-3-CHLOROTETRAHYDRO-2H-INDAZOLES COMPOSITION CONTAINING THEM, AND HERBICIDAL METHOD OF USING THEM

[75] Inventors: Toru Haga, Ibaraki; Eiki Nagano, Nishinomiya; Ryo Sato, Toyonaka; Ryo Yoshida, Kawanishi, all of Japan

[73] Assignee: Sumitomo Chemical Co., Ltd., Osaka, Japan

[*] Notice: The portion of the term of this patent subsequent to Jun. 2, 2004 has been disclaimed.

[21] Appl. No.: 698,389

[22] Filed: Feb. 5, 1985

[30] Foreign Application Priority Data

Feb. 10, 1984 [JP] Japan .................. 59-023498

[51] Int. Cl.$^4$ .................. A01N 43/56; C07D 231/56
[52] U.S. Cl. .......................... 71/92; 548/369
[58] Field of Search .................. 548/369; 71/92

[56] References Cited

U.S. PATENT DOCUMENTS

| | | | |
|---|---|---|---|
| 3,476,763 | 11/1969 | Monbaliu et al. | 564/310 |
| 4,059,434 | 11/1977 | Wolf | 548/369 |
| 4,227,009 | 10/1980 | Koch et al. | 71/92 |
| 4,243,408 | 1/1981 | Chan | 71/92 |
| 4,248,618 | 2/1981 | Serban et al. | 71/92 |
| 4,248,619 | 2/1981 | Serban et al. | 71/92 |
| 4,256,482 | 3/1981 | Wittmann et al. | 71/92 |
| 4,261,729 | 4/1981 | Konotsune et al. | 71/92 |
| 4,404,019 | 9/1983 | Uematsu et al. | 564/310 |

FOREIGN PATENT DOCUMENTS 2127410  4/1984  United Kingdom ............... 548/369

*Primary Examiner*—Richard A. Schwartz
*Assistant Examiner*—Kurt G. Briscoe
*Attorney, Agent, or Firm*—Birch, Stewart, Kolasch & Birch

[57] ABSTRACT

A compound of the formula:

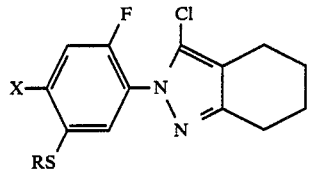

wherein R is a $C_2$-$C_3$ alkyl group, a $C_3$-$C_4$ alkenyl group or a $C_3$-$C_4$ alkynyl group and X is a chlorine atom or a bromine atom, which is useful as a herbicide.

8 Claims, No Drawings

2-SUBSTITUTED PHENYL-3-CHLOROTETRAHYDRO-2H-INDAZOLES COMPOSITION CONTAINING THEM, AND HERBICIDAL METHOD OF USING THEM

The present invention relates to 2-substituted phenyl-3-chlorotetrahydro-2H-indazoles (hereinafter referred to as "3-chlorotetrahydroindazole(s)"), and their production and use.

The present 3-chlorotetrahydroindazoles are represented by the formula:

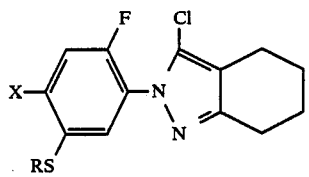

wherein R is a $C_2$–$C_3$ alkyl group, a $C_3$–$C_4$ alkenyl group or a $C_3$–$C_4$ alkynyl group and X is a chlorine atom or a bromine atom. Preferred compounds are those of the formula (I) wherein R is an isopropyl group, an allyl group or a propargyl group. The most preferred compounds are those wherein R is a propargyl group.

It is known that certain kinds of 3-chlorotetrahydroindazoles are effective as herbicides. For instance, the herbicidal use of 3-chloro-2-(2,4-dichloro-5-methoxyphenyl-4,5,6,7-tetrahydro-2H-indazole is disclosed in U.S. Pat. No. 4,059,434. However, the herbicidal effect of this compound is not necessarily satisfactory.

It has now been found that the 3-chlorotetrahydroindazoles (I) exhibit a strong herbicidal activity against a wide variety of weeds including broad-leaved weeds and Graminaceous weeds in an agricultural plowed field by foliar or soil treatment and do not produce any material phytotoxicity on various agricultural crops (i.e. corn, wheat, soybean). Examples of broad-leaved weeds are slender amaranth (*Amaranthus grdacilis*), radish (*Raphanus sativus*), hemp sesbania (*Sesbania exaltata*), sicklepod (*Cassia obtusifolia*), velvetleaf (*Abutilon theophrasti*), prickly sida (*Sida spinosa*), tall morning-glory (*Ipomoea purpurea*), jimsonweed (*Datura stramonium*), black nightshade (*Solanum nigrum*), common cocklebur (*Xanthium strumarium*), common sunflower (*Helianthus annuus*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), oat (*Avena sativa*), etc.

Particularly notable is that the 3-chlorotetrahydroindazoles (I) exert a high herbicidal activity against paddy field weeds including Graminaceous weeds such as barnyardgrass (*Echinochloa oryzicola*), broad-leaved weed such as common falsepimpernel (*Lindernia procumbens*), indian toothcup (*Rotala indica*) and waterwort (*Elatine triandra*), Cyperaceous weeds such as hardstem bulrush (*Scirpus juncoides*) and needle spike-rush (*Eleocharis acicularis*), and arrowhead (*Sagittaria pygmaea*) without any resulting phytotoxicity to rice plants on flooding treatment. Their selectivity to rice plants in a paddy field on flooding treatment is excellent.

Accordingly, the 3-chlorotetrahydroindazoles (I) can be used as herbicides applicable to agricultural plowed fields as well as paddy fields.

The 3-chlorotetrahydroindazole (I) is obtained by reacting the corresponding hexahydroindazol-3-one of the formula:

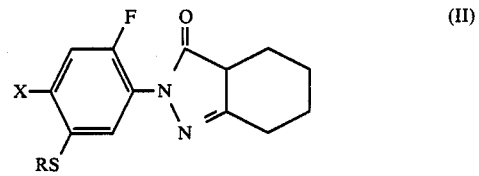

wherein R and X are each as defined above with a chlorinating agent in a solvent in the presence or absence of a dehydrohalogenating agent at a temperature of 80° to 200° C. under an ordinary pressure to 50 kg/cm² for a period of 1 to 240 hours.

The chlorinating agent and the dehydrohalogenating agent may be used respectively in amounts of 1.0 equivalent to a large excess and of a trace to 1.0 equivalent to 1 equivalent of the hexahydroindazol-3-one (II).

Examples of the solvent are aliphatic hydrocarbons (e.g. hexane, ligroin), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diisopropyl ether, dioxane, ethyleneglycol dimethyl ether), esters (e.g. ethyl formate, ethyl acetate, butyl acetate, diethyl carbonate), tertiary amines (e.g. pyridine, triethylamine, N,N-diethylaniline, tributylamine, N-methylmorpholine) and acid amides (e.g. formamide, N,N-dimethylformamide, acetamide), and their mixtures.

As the dehydrohalogenating agent, there may be exemplified organic amines such as pyridine, triethylamine, N,N-diethylaniline, etc. Examples of the chlorinating agents are phosphorus oxychloride, thionyl chloride, oxalyl chloride, phosgene, trichloromethyl chloroformate, etc.

The reaction mixture is usually subjected to post-treatment such as washing with water, extraction with a solvent and concentration, although it varies depending on the kind of the chlorinating agent used. When desired, the recovered product may be purified by a per se conventional procedure such as column chromatography, distillation or recrystallization.

Typical examples of the 3-chlorotetrahydroindazole (I) are as follows:

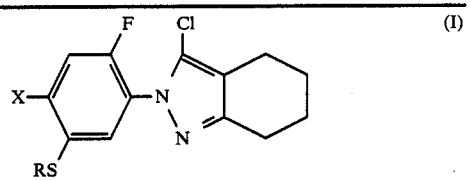

| X  | R |
|----|---|
| Cl | —CH$_2$CH$_3$ |
| Cl | —CH$_2$CH$_2$CH$_3$ |
| Cl | —CH(CH$_3$)$_2$ |
| Cl | —CH$_2$CH=CH$_2$ |
| Cl | —CH$_2$C≡CH$_2$ <br> $\quad\;\;$ \| <br> $\quad\;\;$ CH$_3$ |

-continued

| X | R |
|---|---|
| Cl | —CH₂CH=CHCH₃ |
| Cl | —CHCH=CH₂<br>  |<br>  CH₃ |
| Cl | —CH₂C≡CH |
| Cl | —CH₂C≡CCH₃ |
| Cl | —CHC≡CH<br>  |<br>  CH₃ |
| Br | —CH₂CH₃ |
| Br | —CH₂CH₂CH₃ |
| Br | —CH₂CH=CH₂ |
| Br | —CH₂C≡CH |
| Br | —CHC≡CH<br>  |<br>  CH₃ |

Practical and presently preferred embodiments of the production of the 3-chlorotetrahydroindazoles (I) are illustratively shown in the following example.

EXAMPLE 1

To a solution of trichloromethyl chloroformate (50 ml) in toluene (500 ml), active carbon (2 g) was added, and the resulting mixture was allowed to stand overnight. After removal of active carbon by filtration, a solution of 2-(4-chloro-2-fluoro-5-isopropylthio)phenyl-4,5,6,7-tetrahydro-2H-indazole-3-one (4.95 g) in toluene (20 ml) was added thereto, and the resultant mixture was heated under reflux for 3 hours. Toluene was removed from the reaction mixture by distillation, and the residue was purified by silica gel column chromatography using a mixture of ethyl acetate and n-hexane as an eluent to give 2.0 g of 3-chloro-2-(4-chloro-2-fluoro-5-isopropylthio)phenyl-4,5,6,7-tetrahydro-2H-indazole (Compound No. 1). $n_D^{29.7}$ 1.5882.

Examples of the 3-chlorotetrahydroindazole (I) produced in the same manner as above are shown in Table 1.

TABLE 1

| Compound No. | X | R | Physical property |
|---|---|---|---|
| 1 | Cl | —CH(CH₃)₂ | $n_D^{29.7}$ 1.5882 |
| 2 | Cl | —CH₂CH₂CH₃ | $n_D^{13.5}$ 1.5952 |
| 3 | Cl | —CH₂CH=CH₂ | M.P. 58.2° C. |
| 4 | Cl | —CH₂C≡CH | M.P. 137.2° C. |
| 5 | Br | —CH₂C≡CH | M.P. 138–139.5° C. |

Production of the starting hexahydroindazol-3-one (II) is schematically shown below:

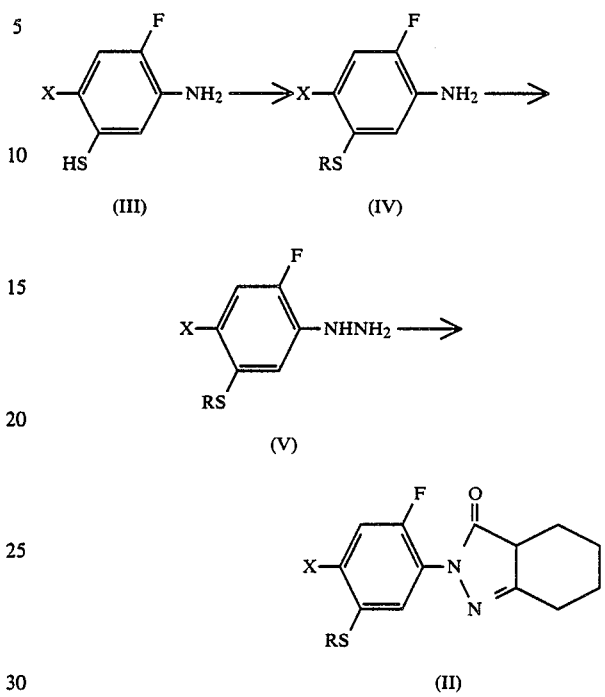

wherein R and X are each as defined above.

Namely, the aminothiol (III) is reacted with a halide of the formula: Y-R in which Y is a chlorine atom, a bromine atom or an iodine atom and R is as defined above to give the aminosulfide (IV). The reaction is carried out in water in the presence of an inorganic base (e.g. sodium hydroxide, potassium hydroxide) in the presence of a catalytic amount of a phase transfer agent (e.g. triethylbenzylammonium chloride, tributylbenzylammonium chloride) at a temperature of 10° to 40° C. The halide and the inorganic base may be respectively used in amounts of 1.0 to 3.0 equivalents and of 1.0 to 1.5 equivalents to the aminothiol (III).

The aminosulfide (IV) is then reacted with concentrated hydrochloric acid at a temperature of 0° to 40° C., followed by reacting the resultant hydrochloride with 1.0 to 1.5 equivalents of sodium nitrite at −10° to 5° C. to form the diazonium salt. The diazonium salt is reduced with 3.0 to 10 equivalents (in regard to the aminosulfide (IV)) of stannous chloride at 0° to −40° C. to obtain the hydrazine hydrochloride, which is neutralized with an aqueous alkaline solution (e.g. sodium hydroxide, potassium hydroxide, potassium carbonate) to obtain the hydrazine sulfide (V). The thus obtained hydrazine sulfide (V) is reacted with 1.0 to 1.2 equivalents of 2-alkoxycarbonylcyclohexanone in a solvent (e.g. acetic acid, toluene, xylene) at a temperature of 50° to 200° C. (preferably 80° to 150° C.) optionally while dehydration by azeotropic distillation or in the presence of molecular sieve is conducted to give the hexahydroindazol-3-one (II).

The starting aminothiol (III) is readily obtained by treating the acetaminothiophenol of the formula:

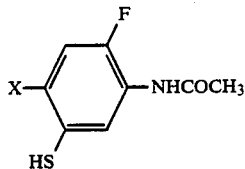

wherein X is as defined above (EP-A-No. 0126419) with a mineral acid (e.g. hydrochloric acid).

Some typical examples of production of the hexahydroindazol-3-one (II) are shown in the following examples.

EXAMPLE 2

To a mixture of 5-amino-2-chloro-4-fluorothiophenol (8.4 g), sodium hydroxide (3 g), water (80 ml), diethyl ether (40 ml) and tributylbenzylammonium chloride (0.1 g), propargyl chloride (5.2 g) was dropwise added at room temperature (ca. 20° to 25° C.), and the resultant mixture was stirred at the same temperature for 3 hours. The water layer was separated and extracted with ether. The ether extract was combined with the ether layer, washed with water, dried and concentrated under reduced pressure. The residue was crystallized from methanol to give 3.25 g of 4-chloro-2-fluoro-5-propargylthioaniline. M.P., 58°–59.5° C.

NMR (CDCl$_3$) δppm: 2.2 (1H, t, J=2 Hz), 3.5 (2H, d, J=2 Hz), 3.7 (2H, broad (NH$_2$)), 6.95 (1H, d, J=8 Hz), 7.05 (1H, d, J=10 Hz).

EXAMPLE 3

4-Chloro-2-fluoro-5-propargylthioaniline (3.25 g) was added to conc. hydrochloric acid (30 ml), and the resultant mixture was stirred at a temperature below 30° C. for 30 minutes. A solution of sodium nitrite (1.1 g) in water (4 ml) was added thereto at 0° C., followed by stirring at the same temperature for 1.3 hours. A saturated aqueous urea solution was added to the mixture for removal excess nitrite ion. A solution of stannous chloride (7 g) in hydrochloric acid (20 ml) was added thereto at a temperature below −30° C. The resultant mixture was stirred at a temperature below 0° C. for 3 hours, and insoluble materials were removed by filtration. The insoluble materials were washed with a small amount of cold water and combined with a 5% sodium hydroxide solution. The mixture was adjusted to a pH of 8 to 10 and extracted with ethyl acetate. The extract was washed with water, dried and concentrated under reduced pressure. The residue was crystallized from n-hexane to give 2.5 g of 4-chloro-2-fluoro-5-propargylthiophenylhydrazine. M.P., 100.2° C.

EXAMPLE 4

A mixture of 4-chloro-2-fluoro-5-propargylthiophenylhydrazine (1.2 g), ethyl 2-cyclohexanonecarboxylate (0.85 g) and acetic acid (10 ml) was heated under reflux for 2 hours, followed by cooling. Water was added thereto, and the resulting mixture was extracted with ethyl acetate. The extract was washed with water and a saturated sodium hydrogen carbonate solution, dried and concentrated. The residue was crystallized from a mixture of n-hexane and ether to give 0.87 g of 2-(4-chloro-2-fluoro-5-propargylthiophenyl)-3,3a,4,5,6,7-hexahydro-2H-indazol-3-one. M.P., 170°–171° C.

IR νcm$^{-1}$ (Nujol): 3060, 2650, 1720, 1620.

As reported in E. Marzin et al: "The Tautomerism of Heterocycles", Academic Press (1976), the above product forms and comprises the tautomers as shown below:

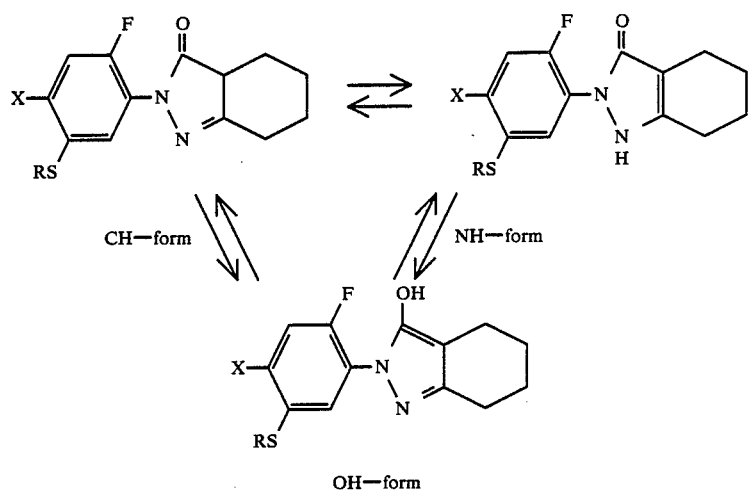

wherein R and X are each as defined above.

Still, the chlorination of the hexahydroindazol-3-one (II) to the 3-chlorotetrahydroindazole (I) proceeds through the OH-form, and under the reaction conditions of chlorination as stated above, the OH-form is present predominantly. Accordingly, a mixture of the tautomers may be as such subjected to chlorination.

In the practical use of the 3-chlorotetrahydroindazoles (I), they may be applied in any preparation form such as emulsifiable concentrates, wettable powders, suspensions, granules, etc. in combination with conventional solid or liquid carriers or diluents as well as surface active agents or auxiliary agents.

The content of the 3-chlorotetrahydroindazole (I) as the active ingredient in such formulation form is usually within a range of 0.03 to 90% by weight, preferably of 0.05 to 80% by weight.

Examples of the solid carrier or diluent are kaolin clay, attapulgite clay, bentonite, terra alba, pyrophyllite, talc, diatomaceous earth, calcite, walnut powders, urea, ammonium sulfate, synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts are by weight. The compound number of the active ingredient corresponds to the one in Table 1.

FORMULATION EXAMPLE 1

Fifty parts of Compound No. 5, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Ten parts of Compound No. 1, 14 parts of polyoxyethylenestyrylphenyl ether, 6 parts of calcium dodecylbenzenesulfonate, 30 parts of xylene and 40 parts of isophorone are well mixed while being powdered to obtain an emulsifiable concentrate.

FORMULATION EXAMPLE 3

Two parts of Compound No. 4, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 1 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

The 3-chlorotetrahydroindazoles (I) thus formulated in any suitable form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the 3-chlorotetrahydroindazoles (I) over the top of the plants. It may also be applied directly to the weeds if care is taken to keep the chemical off the crop foliage.

The 3-chlorotetrahydroindazoles (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the 3-chlorotetrahydroindazoles (I) can be used as herbicides applicable to agricultural plowed fields as well as paddy fields. They are also useful as herbicides to be employed for orchard, pasture land, lawn, forest, non-agricultural field, etc.

The dosage rate of the 3-chlorotetrahydroindazoles (I) may vary on prevailing weather conditions, formulation used, prevailing season, mode of application, soil involved, crop and weed species, etc. Generally, however, the dosage rate is from 0.002 to 100 grams, preferably from 0.08 to 40 grams, of the active ingredient per are. The herbicidal composition of the present invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the 3-chlorotetrahydroindazoles (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 2 below were used for comparison.

TABLE 2

| Compound No. | Chemical structure | Remarks |
|---|---|---|
| A | 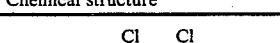 | U.S. Pat. No. 4,059,434 |

TABLE 2-continued

| Compound No. | Chemical structure | Remarks |
|---|---|---|
| B | 2-Cl, 4-$CF_3$-phenyl-O-phenyl(2-COONa, 4-$NO_2$) | Commercially available herbicide; "acifluorufensodium" |
| C | 4-Cl, 2-F, 5-(CH≡C-$CH_2$O)-phenyl-N(pyrazole fused cyclohexene, 3-Cl, 3a-F) | GB-2127410A |

TEST EXAMPLE 1

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and hardstem bulrush and the statoblast of needle spikerush were sowed in 1 to 2 cm depth. Water was poured therein to make a flooded condition. Rice seedlings of the 3-leaf stage were transplanted therein and grown in a greenhouse. Four days (at that time barnyardgrass started to germinate) thereafter, a designated amount of the test compound formulated in an emulsifiable concentrate according to Formulation Example 2 and diluted with water (10 ml) was applied to the pots by perfusion, followed by addition of water thereto to make a 4 cm depth. The test plants were grown for a further 20 days in the greenhouse, and the herbicidal activity was examined. The results are shown in Table 3.

TABLE 3

| Compound No. | Dosage (g/are) | Rice plant | Barn-yard grass | Broad-leaved weeds | Needle spikerush | Hardstem bulrush |
|---|---|---|---|---|---|---|
| 1 | 0.32 | 1 | 5 | 5 | 5 | 4 |
|   | 0.16 | 0 | 5 | 5 | 4 | — |
|   | 0.08 | 0 | 4 | 5 | 4 | — |
| 3 | 0.32 | 1 | 5 | 5 | 5 | 4 |
|   | 0.16 | 0 | 5 | 5 | 4 | — |
|   | 0.08 | 0 | 4 | 5 | 4 | — |
| 4 | 0.32 | 1 | 5 | 5 | 5 | 5 |
|   | 0.16 | 1 | 5 | 5 | 5 | 4 |
|   | 0.08 | 0 | 5 | 5 | 4 | — |
| 5 | 0.32 | 1 | 5 | 5 | 5 | 5 |
|   | 0.16 | 1 | 5 | 5 | 5 | 4 |
|   | 0.08 | 0 | 5 | 5 | 4 | — |
| A | 0.32 | 2 | 3 | 5 | 3 | 2 |
|   | 0.16 | 0 | 1 | 4 | 2 | 0 |
|   | 0.08 | 0 | 0 | 2 | 0 | 0 |

TEST EXAMPLE 2

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and hardstem bulrush and the statoblast of needle spikerush were sowed in 1 to 2 cm depth. Water was poured therein to make a flooded condition. Rice seedlings of the 3-leaf stage were transplanted therein and grown in a greenhouse. Eleven days (at that time barnyardgrass grew to 2-left stage) thereafter, a designated amount of the test compound formulated in an emulsifiable concentrate according to Formulation Example 2 and diluted with water (10 ml) was applied to the pots by perfusion, followed by addition of water thereto to make a 4 cm depth. The test plants were grown for further 20 days in the greenhouse, and the herbicidal activity was examined. The results are shown in Table 4.

TABLE 4

| Compound No. | Dosage (g/are) | Rice plant | Barn-yard grass | Broad-leaved weeds | Needle spikerush | Hardstem bulrush |
|---|---|---|---|---|---|---|
| 1 | 0.32 | 1 | 5 | 5 | 4 | 4 |
|   | 0.16 | 0 | 4 | 5 | 4 | — |
|   | 0.08 | 0 | — | 4 | — | — |
| 5 | 0.32 | 1 | 5 | 5 | 4 | 4 |
|   | 0.16 | 0 | 5 | 5 | 4 | — |
|   | 0.08 | 0 | 4 | 5 | — | — |
| A | 0.32 | 0 | 4 | 5 | 2 | 1 |
|   | 0.16 | 0 | 0 | 2 | 1 | 0 |
|   | 0.08 | 0 | 0 | 0 | 0 | 0 |

TEST EXAMPLE 3

Vats (33 cm × 23 cm × 11 cm) were filled with upland field soil, and the seeds of corn, wheat, barnyardgrass (*Echinochloa cruss-galli*), green foxtail, cotton, soybean, common cocklebur, velvetleaf, tall morningglory, slender amaranth and black nightshade were sowed therein and cultivated for 18 days in a greenhouse. A designated amount of the test compound formulated in an emulsifiable concentrate according to Formulation Example 2 was diluted with water containing a spreading agent, and the dilution was sprayed onto the foliage of the test plants by means of a small hand sprayer at a spray volume of 5 liters per are. At the time of the application, the growing stage of the test plants varied depending on their species, but they were generally at the 1 to 4 leaf stage and in a height of 2 to 12 cm. The test plants were further grown in the greenhouse for 20 days, and the herbicidal activity was examined. The results are shown in Table 5.

TABLE 5

| Compound No. | Dosage (g/are) | Corn | Wheat | Barnyard grass | Green foxtail | Cotton | Soybean | Common cocklebur | Velvet leaf | Tall morning-glory | Slender amaranth | Black night shade |
|---|---|---|---|---|---|---|---|---|---|---|---|---|
| 1 | 0.32 | — | — | 4 | 5 | 5 | 3 | 5 | 5 | 5 | 5 | 5 |
|   | 0.16 | 2 | 1 | 3 | 4 | 5 | 2 | 4 | 5 | — | 5 | 5 |
|   | 0.08 | 0 | 0 | — | — | 4 | 2 | — | 5 | — | 5 | 5 |
| 5 | 0.32 | — | — | 5 | 5 | 5 | 4 | 5 | 5 | 5 | 5 | 5 |
|   | 0.16 | 2 | 1 | 4 | 4 | 5 | 3 | 5 | 5 | 5 | 5 | 5 |
|   | 0.08 | 1 | 1 | — | 4 | 5 | 1 | 5 | 5 | 5 | 5 | 5 |
| B | 1.25 | 1 | 1 | 1 | 2 | 4 | 2 | 3 | 3 | 4 | 5 | 4 |
|   | 0.32 | 0 | 0 | 0 | 0 | 2 | 1 | 1 | 1 | 2 | 3 | 2 |

TEST EXAMPLE 4

Cylindrical plastic pots (diameter, 10 cm; height, 10 cm) were filled with upland field soil, and the seeds of green foxtail, soybean, common cocklebur, tall morningglory and common sunflower were sowed therein and covered with soil. A designated amount of the test compound formulated in an emulsifiable concentrate according to Formulation Example 2 was diluted with water, and the dilution was sprayed onto the soil by means of a small hand sprayer at a spray volume of 10 liters per are, followed by mixing of the soil to the depth of 4 cm. The test plants were further grown in the greenhouse for 20 days, and the herbicidal activity was examined. The results are shown in Table 6.

TABLE 6

| Compound No. | Dosage (g/are) | Green foxtail | Soybean | Common cocklebur | Tall morning-glory | Common sunflower |
|---|---|---|---|---|---|---|
| 1 | 40 | 5 | 1 | 5 | 5 | 4 |
|   | 20 | 4 | 1 | — | 4 | — |
| 2 | 40 | 5 | 1 | 4 | 4 | 4 |
|   | 20 | 4 | 1 | — | 3 | 2 |
| 3 | 40 | 5 | 1 | 5 | 5 | 4 |
|   | 20 | 4 | 1 | — | 4 | 3 |
| 4 | 40 | 5 | 2 | 5 | 5 | 5 |
|   | 20 | 5 | 1 | 4 | 5 | — |
| 5 | 40 | 5 | 2 | 5 | 5 | 5 |
|   | 20 | 5 | 1 | 4 | 5 | — |
| A | 40 | 4 | 1 | 2 | 2 | 1 |
|   | 20 | 1 | 0 | 0 | 2 | 0 |

TEST EXAMPLE 5

Wagner's pots (1/5000 are) were filled with paddy field soil, and the seeds of barnyardgrass (*Echinochloa oryzicola*) and broad-leaved weeds (i.e. common falsepimpernel, indian toothcup, waterwort) were sowed in 1 to 2 cm depth. Water was poured therein to make a flooded condition. Rice seedlings at the 1.5-leaf stage were transplanted to the pots, and cultivation as carried out in a greenhouse for 4 days. A designated amount of the test compound formulated in an emulsifiable concentrate according to Formulation Example 2 was diluted with water (10 ml), and the dilution was applied to the pots by perfusion. The test plants were grown for a further 20 days in the greenhouse, and the herbicidal activity was examined. For two days from the application, water was leaked with a 3 cm depth per day. The results are shown in Table 7.

TABLE 7

| Compound No. | Dosage (g/are) | Rice plant | Barnyard grass | Broad-leaved weeds |
|---|---|---|---|---|
| 5 | 16 | 2 | 5 | 5 |
|   | 4 | 0 | 5 | 5 |
|   | 1 | 0 | 5 | 5 |
| C | 4 | 2 | 5 | 5 |
|   | 1 | 0 | 5 | 5 |
|   | 0.25 | 0 | 3 | 4 |

What is claimed is:

1. A compound of the formula:

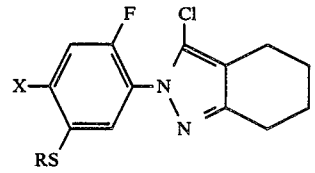

wherein R is a $C_2$-$C_3$ alkyl group, a $C_3$-$C_4$ alkynyl group or a $C_3$-$C_4$ alkenyl group and X is a chlorine atom or a bromine atom.

2. The compound according to claim 1, wherein R is an isopropyl group, an allyl group or a propargyl group.

3. The compound according to claim 2, wherein R is a propargyl group.

4. The compound according to claim 1, which is 3-chloro-2-(4-chloro-2-fluoro-5-propargylthio)phenyl-4,5,6,7-tetrahydro-2H-indazole.

5. The compound according to claim 1, which is 3-chloro-2-(4-chloro-2-fluoro-5-isopropylthio)phenyl-4,5,6,7-tetrahydro-2H-indazole.

6. A herbicidal composition which comprises as an active ingredient a herbicidally effective amount of the compound according to claim 1, and an inert carrier or diluent.

7. A method of controlling weeds which comprises applying a herbicidally effective amount of the compound according to claim 1, to the area where the weeds grow or will grow.

8. The method according to claim 7, wherein the area is the paddy field of rice plant.

* * * * *